United States Patent [19]

Young

[11] Patent Number: 4,966,620

[45] Date of Patent: * Oct. 30, 1990

[54] METHODS FOR FACILITATING THE HARVEST OF FOOD CROPS

[75] Inventor: Donald C. Young, Fullerton, Calif.

[73] Assignee: Union Oil Company of California, Los Angeles, Calif.

[*] Notice: The portion of the term of this patent subsequent to Apr. 4, 2006 has been disclaimed.

[21] Appl. No.: 305,847

[22] Filed: Feb. 2, 1989

Related U.S. Application Data

[63] Continuation of Ser. No. 918,546, Oct. 10, 1986, abandoned, which is a continuation-in-part of Ser. No. 455,268, Jan. 3, 1983, Pat. No. 4,818,269, and a continuation-in-part of Ser. No. 445,317, Jan. 3, 1983, Pat. No. 4,460,733, and a continuation-in-part of Ser. No. 442,269, Nov. 17, 1982, abandoned, and a continuation-in-part of Ser. No. 444,667, Nov. 26, 1982, abandoned, and a continuation-in-part of Ser. No. 453,282, Dec. 27, 1982, Pat. No. 4,522,644, and a continuation-in-part of Ser. No. 453,496, Dec. 27, 1982, now Defensive Publication No. 4,910,179.

[51] Int. Cl.$^5$ .................... A01N 59/00; A01N 31/00
[52] U.S. Cl. ............................................ 71/83; 71/72
[58] Field of Search ................................... 71/72, 83

[56] References Cited

U.S. PATENT DOCUMENTS

| | | | |
|---|---|---|---|
| Re. 1,995 | 6/1865 | Hoffman | 127/36 |
| 1,340,708 | 5/1920 | Fjellanger | 71/28 |
| 1,878,852 | 9/1932 | Hoppler et al. | 127/36 |
| 1,884,105 | 11/1932 | Moore | 423/549 |
| 1,917,539 | 8/1933 | Miles | 127/37 |
| 1,919,623 | 8/1933 | Dreyfus | 127/37 |
| 2,767,108 | 10/1956 | Fetzer | 127/34 |
| 2,978,359 | 4/1961 | Wedell | 141/138.8 |
| 3,432,482 | 3/1969 | Ohfuka et al. | 260/85.5 |
| 3,459,499 | 4/1970 | Mullen, Jr. | 423/313 |
| 3,558,530 | 1/1971 | Schroder et al. | 260/2.5 |
| 3,660,070 | 5/1972 | Maruta et al. | 71/28 |
| 3,778,431 | 12/1973 | Knightlinger et al. | 260/233.3 R |
| 3,816,375 | 6/1974 | Bozer et al. | 260/67 FA |
| 3,873,734 | 3/1975 | Higgins et al. | 71/28 |
| 3,878,304 | 4/1975 | Moore | 1/14 |
| 3,918,952 | 11/1975 | Neumiller | 71/28 |
| 4,116,664 | 9/1978 | Jones | 71/28 |
| 4,214,888 | 10/1981 | Young | 71/29 |
| 4,310,343 | 1/1982 | Verdegaal et al. | 71/28 |
| 4,315,763 | 2/1982 | Stoller et al. | 71/29 |
| 4,397,675 | 8/1983 | Young | 71/28 |
| 4,402,852 | 9/1983 | Young | 252/182 |
| 4,404,116 | 9/1983 | Young | 252/182 |
| 4,439,348 | 3/1984 | Akerberg | 252/426 |
| 4,445,925 | 5/1984 | Young | 71/28 |
| 4,447,253 | 5/1984 | Young | 71/28 |
| 4,451,577 | 5/1984 | Coss | 502/167 |
| 4,474,925 | 10/1984 | Sartoretto et al. | 71/119 |
| 4,512,813 | 4/1985 | Young | 134/27 |
| 4,522,644 | 6/1985 | Young | 71/78 |
| 4,589,925 | 5/1986 | Young | 134/3 |
| 4,626,417 | 5/1986 | Young | 127/37 |
| 4,664,717 | 12/1986 | Young | 423/235 |
| 4,673,522 | 6/1987 | Young | 252/87 |
| 4,686,017 | 8/1987 | Young | 204/45.1 |
| 4,722,986 | 2/1988 | Young | 527/203 |
| 4,743,669 | 5/1988 | Young | 204/45.1 |
| 4,755,265 | 7/1988 | Young | 204/45.1 |
| 4,801,511 | 1/1989 | Young | 429/198 |
| 4,818,269 | 4/1989 | Young | 71/83 |
| 4,831,056 | 5/1989 | Young | 71/28 |
| 4,834,788 | 5/1989 | Young | 71/83 |

OTHER PUBLICATIONS

Science News, vol. 123, No. 23, Jun. 4, 1983, p. 366; Science Service, Inc., 1719 N St. N.W., Washington, D.C., "Cellulos Digestion by Lab Bacteria".

Title 40, Code of Federal Regulations, Section 180.1019, "Sulfuric Acid; Exemption from the Requirement of Tolerance".

Chemical Abstracts, 93, 93:90069b; "Effects of Herbicidal Weed Control on Growth and Development of Ground Nuts (Arachis hypogaea 1) in Western Kenya", Adalla, Proceedings of the East African Weed Science Confer, 6, 1976, published 1977.

"Incidental Uses of Fertilizers, Urea, and Muriate of Potash in Mature and Immature Oil Palm Plantings; Some Preliminary Results," Chan, Int. Dev. Oil Palm Proceedings, Malaysian International Agricultural Oil Palm Conference, 1977.

"The Sensitivity of Weeds and Cotton to the Herbicide Toluin in Dependence on the Form of Nitrogen Fetilizers Used," Kamilova et al., The Institute of Experimental Plant Biology of the Academy Agrokhimiya, No. 5, 1980, pp. 124–127.

Farm Chemicals Handbook, Meister Publishing Company, Willoughby, Ohio, 1981, p. C-316.

Bach et al., Chemical Abstract 95:37118g (1981).

The Condensed Chemical Dictionary, Seventh Edition, Van Nostrand Reinhold Company, New York, 1969, p. 908.

"Organic Chemistry of Bivalent Sulfur," Chemical Publishing Company, 1962, pp. 14, 15, 94 and 95.

"The Chemistry of Carboxylic Acids and Esters," Interscience Publishers, 1969, pp. 732, 733, 758 and 759.

Lohry, "Techniques of Manufacturing Hot Mix Suspensions," National Fertilizer Solutions Assn. Round Up papers, 1968, pp. 34–38.

D. F. duToit, Verslag Akad. Wetenschappen, 22, 573–4 (abstracted in Chemical Abstracts, 8, 2346, 1914).

L. H. Dalman, "Ternary Systems of Urea and Acid. I. Urea, Nitric Acid, and Water, II, Urea, Sulfuric Acid and Water, III, Urea, Oxalic Acid and Water"; JACS, 56, 549–53 (1934).

Sulfur Institute Bulletin No. 10 (1964), "Adding Plant Nutrient Sulfur to Fertilizer".

Kirk–Othmer Encyclopedia of Chemical Technology, Third Edition, John Wiley and Sons, New York, 1980.

Primary Examiner—Richard L. Raymond
Assistant Examiner—Eric J. Kraus
Attorney, Agent, or Firm—Gregory F. Wirzbicki; Michael H. Laird

[57] ABSTRACT

Methods are provided for facilitating the harvest of food crops by applying to the crop foliage an amount of an aqueous solution containing a combination of urea and sulfuric acid in which the urea/$H_2SO_4$ molar ratio is within the range of about ¼ to about 7/4 sufficient to desiccate the foliage prior to harvest.

15 Claims, No Drawings

METHODS FOR FACILITATING THE HARVEST OF FOOD CROPS

RELATED APPLICATION

This application is a continuation of U.S. application Ser. No. 06/918,546, filed Oct. 10, 1986, now abandoned, which is a continuation-in-part of my copending applications U.S. Ser. No. 455,268, Cellulosic Composition and Methods for Treating Cellulosic Materials, filed Jan. 3, 1983, now U.S. Pat. No. 4,818,269; U.S. Ser. No. 455,317, Plant Seed Compositions and Methods for Treating Plant Seeds, filed Jan. 3, 1983, now U.S. Pat. No. 4,460,733; U.S. Ser. No. 442,296, Systemic Herbicidal Compositions and Methods of Use, filed Nov. 17, 1982; now abandoned U.S. Ser. No. 444,667, Methods for Controlling Vegetation, filed Nov. 26, 1982; now abandoned U.S. Ser. No. 453,282, Methods for Selectively Controlling Plant Suckers, filed Dec. 27, 1982; now U.S. Pat. No. 4,522,644; and U.S. Ser. No. 453,496, Acid-Catalyzed Reactions and Compositions for Use Therein, filed Dec. 27, , now U.S. Pat. No. 4,910,179.

BACKGROUND

1. Field of the Invention

This invention relates to methods for desiccating the foliage of food crops and, in particular, to methods for facilitating the harvest of food crops.

2. Introduction

A wide variety of food crop plants have abundant foliage which interferes with and increases the cost of crop harvest, particularly with mechanical harvesters. A variety of methods and compositions have been devised to desiccate foliage sufficiently to facilitate harvest. As used herein, "desiccating" is used in the agricultural sense which typically means reducing the above-ground biomass sufficiently to reduce interference with harvest rather than in the strict chemical sense of the word. In chemical terminology, desiccation usually connotes removal of water by chemical action. Sugar cane and other crops, the produce of which is not harmed by fire, have been flame-defoliated, although this procedure now is banned in a many areas to control air pollution. A variety of chemical desiccants have been employed to reduce the mass and improve the manageability of crop plant foliage. Illustrative are sodium chlorate, endothall, arsenic acid, and secondary butyl-2,4-dinitrophenol sold as Dinoseb®, Synox®, and under other designations.

Sulfuric acid applied at sufficiently high dosage rates desiccates crop vegetation, but the use of sufficiently strong sulfuric acid at sufficiently high rates presents several significant problems. Sulfuric acid damages the harvestable portion of many crops by oxidation and/or dehydration reactions characteristic of sulfuric acid. Furthermore, sulfuric acid dosage rates required to achieve rapid foliage desiccation are substantial since the acid is consumed by reaction with foliage by oxidation and/or dehydration, and the hazards associated with the use of large volumes of concentrated sulfuric acid are well known and require great care in application, sophisticated, expensive application equipment, and protective personnel clothing and devices. Furthermore, the use of such volumes of sulfuric acid can result in soil over-acidification and ecotoxic effects associated with acid run-off. Other chemical harvesting aids, such as the desiccants mentioned above, also suffer from one or more disadvantages. Several are relatively expensive, and all are potentially toxic. Some are translocated to the harvestable portion of food crops with obvious, undesirable effects. For instance, arsenic acid is very toxic both to plants and the environment and can contaminate both the harvestable food product and the environment. Sodium chlorate results in the addition of both sodium and chlorine to the crop and soil, both of which are undesirable. It is also explosive and difficult to handle. Secondary butyl-2,4-dinitrophenol has been identified, in recent studies, as a carcinogen, oncogen, and teratogen. The relatively slow activity of several of the chemical desiccants is also disadvantageous since it is generally desirable to harvest the crop as soon as possible after preharvest treatment, i.e., within 24 hours or less. However, some harvest aids, such as secondary butyl-2,4-dinitrophenol require days or weeks to desiccate plant foliage sufficiently to facilitate harvest, depending upon the crop type and field conditions. Furthermore, the residual toxicity of several chemical harvest aids prevents entry of personnel into treated fields due to toxic chemical residue on plant foliage.

The desirability of harvesting as soon as possible after preharvest treatment is due to several factors, and potatoes and sugar beets are classic illustrations. In these and other crops, it is preferable to foster productive growth of the crop until harvest. Destruction of plant foliage obviously deters or terminates that process, and the lapse of any significant time between preharvest treatment and harvest results in a proportionate economic loss to the grower and increases the risk of crop spoilage.

Accordingly, a need exists for a nontoxic, fastacting, relatively inexpensive harvest aid that rapidly desiccates living food crop foliage sufficiently to facilitate harvest.

SUMMARY OF THE INVENTION

It has now been found that food crop harvest can be facilitated by applying to the plant foliage an aqueous solution containing a combination of urea and sulfuric acid in which the urea/$H_2SO_4$ molar ratio is within the range of about ¼ to about 7/4. In such solutions, at least about 25 percent of the sulfuric acid is present as the monourea adduct of sulfuric acid since urea any sulfuric acid react to form one of two possible adducts essentially immediately at ambient temperatures and above. Such compositions are fast-acting, and they are nontoxic and relatively noncorrosive to personnel, equipment, and the environment in comparison to other preharvest aids. Their application to plant foliage does not result in the translocation of any toxic material to the food product or the persistence of toxic residues on plant foliage or in the environment. On the contrary, their use results in the addition of nutrient nitrogen and sulfur to the soil. In particular, the useful compositions are more active for desiccating plant foliage than is sulfuric acid on an equivalent $H_2SO_4$ basis, and they are much easier to handle and present much less risk of damage to harvestable plant parts than does sulfuric acid.

DETAILED DESCRIPTION OF THE INVENTION

Briefly, the invention provides methods for facilitating the harvest of food crops and for harvesting such crops which involve applying to the foliage of crop plants an aqueous solution containing a combination of urea and sulfuric acid in which the urea/H$_2$SO$_4$ molar ratio is within the range of about ¼ to about 7/4. These methods can be employed to facilitate the harvest of all types of food crops in which harvesting is simplified or otherwise benefited by desiccating the foliage shortly before harvest and thereby reducing the interference of plant foliage with harvesting personnel or machinery. The methods are particularly suitable for preharvest treatment of tuberous crops such as potatoes, beets, and the like, and they can be employed with a variety of fruit and vegetable crops as well. Illustrative crops include grapes, berry crops, tomatoes, particularly tomatoes intended for the manufacture of tomato-derived products, squash, melons, potatoes, cotton, beans and peas, particularly soybeans, grains (especially milo), peanuts, sugar cane, all varieties of beets (sugar beets in particular), hops, peppers, etc. The methods are particularly useful for facilitating harvest and promoting rapid desiccation of foliage on tuberous crops that typically have abundant foliage, such as potatoes, beets, and the like.

The useful urea-sulfuric acid harvesting aids are aqueous solutions containing a combination of urea and sulfuric acid, in the presence or absence of other components, in which the urea/ H$_2$SO$_4$ molar ratio is within the range of about ¼ to about 7/4. These relative proportions of urea and sulfuric acid ensure that at least a portion of the sulfuric acid is present as the monourea adduct of sulfuric acid. I have found that the monourea adduct of sulfuric acid efficiently and rapidly desiccates the foliage on a wide variety of plants and does so in the absence of undesirable reactions such as oxidation and dehydration associated with sulfuric acid which consume the acid per se and can damage the harvestable portion of the crop. The monourea adduct is not present in compositions in which the urea/H$_2$SO$_4$ molar ratio is 2 or more. In such compositions, all of the sulfuric acid is present as the diurea adduct. The diurea adduct of sulfuric acid is much less effective than the monourea adduct for promoting foliage desiccate. Accordingly, the more preferred compositions are those in which a higher proportion of the sulfuric acid is present as the monourea adduct, e.g., compositions which have urea/H molar ratios within the range of about ½ to about 3/2, most preferably about 1/1 to about 3/2. In the latter case, all of the sulfuric acid is present as either the mono- or diurea adduct, and at least 50 percent is present as the monourea adduct.

Very minor concentrations of urea and sulfuric acid are capable of producing significant desiccation of plant foliage. Thus, aqueous solutions in which the urea and sulfuric acid, in combination, constitute about 1 weight percent or more of the composition can be employed. Higher concentrations generally promote more rapid desiccation and reduce the risk of solution run-off from plant foliage (and loss of active material). Accordingly, solutions in which the urea and sulfuric acid, in combination, constitute at least about 5 weight percent of the solution are preferred, while solutions containing 10 percent of the combination of urea and sulfuric acid are most preferred, particularly when lower spray volumes are desired. The urea-sulfuric acid component is very soluble in water, and high concentrations can be employed, although high-pressure spray equipment is often required to apply compositions containing more than 50 percent of the urea-sulfuric acid combination due to its relatively high viscosity. Thus, the urea and sulfuric acid, in combination, typically constitute about 5 to about 80 weight percent of the solution.

The urea-sulfuric acid solutions may optionally contain other components which do not negate the desiccating activity of those compositions. Surfactants and solvents other than water increase the activity of these compositions and generally accelerate foliage desiccation under otherwise identical treatment conditions. The presence of surfactants and/or solvents other than water (i.e., in addition to water) is particularly preferred for the treatment of foliage which contains hydrophobic substances such as lignins, waxy cuticle, and/ or fatty materials such as lipids. Illustrative solvents include organic and inorganic solvents in which both urea and sulfuric acid are miscible (in the aqueous solution) such as dimethyl sulfoxide, alcohols, e.g., methanol, glycol, acetone, methylethyl ketone, tetrahydrofuran, and the like. One or more of such solvents can be present over a wide range of concentrations, usually within the range of about 2 to about 95 weight percent based on the combined weight of solvent, urea, sulfuric acid, and water. Illustrative suitable surfactants are discussed in my copending application, Ser. No. 453,496, referred to above, which is incorporated herein by reference in its entirety. Surfactants can also be employed over a wide range of concentrations. Useful concentrations are usually at least about 0.1 and generally about 0.1 to about 10 weight percent surfactant based on the combined weight of surfactant, urea, sulfuric acid, water, and solvent (if present).

The urea-sulfuric acid components can be prepared by any one of the variety of procedures. One suitable procedure for preparing urea-sulfuric acid components free of thermal decomposition products is disclosed in my U.S. Pat. No. 4,445,925, which is incorporated herein by reference in its entirety. The urea-sulfuric acid component can also be obtained by gradually adding urea to sulfuric acid or vice versa, in the presence or absence of water and/or other solvent. Sufficient cooling must be provided to ensure that the urea-sulfuric acid component does not thermally decompose. As disclosed in my U.S. Pat. No. 4,445,925, the urea-sulfuric acid compositions can decomposed at temperatures below their explosive decomposition temperature. Significant decomposition begins to occur at about 176° F. Moreover, such thermal decomposition often results in the formation of undesirable toxic materials such as sulfamic acid and/or ammonium sulfamate which are known herbicides and can impair the quality of the harvested crop. Generally, the presence of such toxic components is not preferred. Moreover, the decomposition of sulfuric acid and urea reduces the concentration of active components in the composition and is further undesirable for that reason.

The described solutions are applied to the foliage of food crop plants prior to harvest at dosage rates sufficient to facilitate harvest by foliage desiccation. Even at very minor dosage rates, these compositions rapidly desiccate foliage to an extent sufficient to significantly reduce foliage interference with the harvesting effort within 48 hours or less. Higher dosage rates can be employed to achieve significant foliage desiccation within 24 hours or less, and essentially complete foliage desiccation can be achieved within 4 hours or less as illustrated in the following examples. Generally, the solutions are applied to the foliage at rates corresponding to at least about 20 pounds per acre based on the combined weight of urea and sulfuric acid. More rapid desiccation is obtained at dosage rates of at least about 50 pounds per acre, while rates of at least about 300 pounds per acre rapidly desiccate the foliage of essentially all crop varieties. Typically, dosage rates of about 50 to about 500 pounds per acre are sufficient to significantly facilitate crop harvest within 24 hours or less, while rates of 50 to about 300 pounds per acre rapidly desiccate most food crop foliage.

The optimum combination of solution concentration and dosage rate can be best determined for any combination of food crop and field conditions by treating sample plots of the plant population shortly before harvest with different solutions of varying urea-sulfuric acid component concentration at different dosage rates and selecting the combination of treatment conditions best suited to achieve the desired degree of desiccation in the optimum time.

The aqueous solutions can be applied to the plant foliage with typical agricultural foliage spray apparatus. Spray volume is preferably controlled to effect application of the desired quantity of the urea-sulfuric acid component to the crop foliage without excessive run-off.

The invention is further described by the following examples which are illustrative of specific modes of practicing the invention and are not intended as limiting the scope of the invention as defined by the appended claims.

EXAMPLE 1

The foliage of potato plants ready for harvest can be desiccated sufficiently to minimize foliage interference with potato harvest by spraying the foliage with 75 gallons per acre of an aqueous solution containing urea and sulfuric acid in which the urea and sulfuric acid, in combination, constitute 25 weight percent of the solution and in which the urea/$H_2SO_4$ molar ratio is 1.1. Complete foliage desiccation is evident within 4 hours, and the potato crop can be harvested at that time with minimal interference from the plant foliage.

EXAMPLE 2

The foliage of healthy tomato plants can be desiccated prior to harvest to reduce foliage interference with the harvest by spraying the foliage with 400 gallons per acre of an aqueous solution containing 10 percent of combined urea and sulfuric acid in which the urea/$H_2SO_4$ molar ratio is 1.1. This treatment is sufficient to effect complete foliage desiccation within 12 hours at which time the tomatoes can be harvested with little or no interference from plant foliage.

EXAMPLE 3

Interference of healthy cotton plant foliage with cotton harvest can be significantly reduced by spraying the foliage 24 hours prior to harvest with 200 gallons per acre of an aqueous solution containing 20 weight percent combined urea and sulfuric acid in which the urea/$H_2SO_4$ molar ratio is 1.3.

EXAMPLE 4

The foliage of sugar beets can be completely desiccated within 24 hours by spraying the foliage with 400 gallons per acre of an aqueous solution containing 10 weight percent combined urea and sulfuric acid having a urea/$H_2SO_4$ molar ratio of 1.0.

While particular embodiments of the invention have been described, it will be understood, of course, that the invention is not limited thereto since many modifications can be made, and it is intended to include within this invention any such modifications as will fall within the appended claims.

I claim:

1. A method for facilitating the harvest of food crops which comprises applying to the foliage of said crops an amount of an aqueous solution comprising the monourea adduct of sulfuric acid sufficient to desiccate said foliage.

2. A method for facilitating the harvest of crops which comprises applying to the foliage of said crops an amount of an aqueous solution comprising the monourea adduct of sulfuric acid sufficient to desiccate said foliage, said solution being free of unadducted sulfuric acid.

3. A method for facilitating the harvest of food crops which comprises applying to the foliage of said crops an amount of an aqueous solution comprising the monourea adduct of sulfuric acid sufficient to desiccate said foliage, wherein the molar ratio of equivalent urea to equivalent sulfuric acid is at least one.

4. A method for desiccating the foliage of food crops prior to harvest, which comprises applying to the foliage of said crops an amount of an aqueous solution comprising the monourea adduct of sulfuric acid and a surfactant or solvent other than water, free of unadducted sulfuric acid, sufficient to desiccate said foliage, and harvesting said crop.

5. The method defined in any one of claims 1, 2, 3 or 4, wherein said solution is applied to said foliage at least about 4 hours before the harvest of said crop at a rate sufficient to desiccate said foliage within about 4 hours or less.

6. The method defined in any one of claims 1, 2 or 3, wherein said solution further comprises a member selected from the group consisting of surfactants, solvents other than water, and combinations thereof.

7. The method defined in any one of claims 1, 2, 3 or 4, wherein said solution is free of decomposition products of urea and sulfuric acid.

8. The method defined in any one of claims 1, 2, 3 or 4, wherein said solution is free of sulfamic acid and ammonium sulfamate.

9. The method defined in any one of claims 1, 2, 3 or 4, wherein said solution is applied to said foliage at least about 24 hours before the harvest of said crop at a rate sufficient to desiccate said foliage within about 24 hours or less.

10. The method defined in any one of claims 1 or 4, wherein the equivalent urea/$H_2SO_4$ molar ratio is within the range of 1/1 to about 3/2, and said solution is applied to said foliage at a rate sufficient to desiccate said foliage within about 4 hours or less.

11. The method defined in any one of claims 1, 2, 3 or 4, wherein said food crops comprise vegetable or fruit crops.

12. The method defined in any one of claims 1, 2, 3 or 4, wherein the equivalent urea and sulfuric acid in said solution, in combination, constitute at least about 5 weight percent of said solution, and said solution is applied to said foliage at least about 24 hours before the harvest of said food crop at a rate sufficient to desiccate said foliage within about 24 hours or less.

13. The method defined in any one of claims 1, 2, 3 or 4, wherein said food crop is selected from the group consisting of grapes, berries, potatoes, tomatoes, beets, melons, and squash.

14. The method defined in any one of claims 1, 2, 3 or 4 wherein said food crop is selected from the group consisting of squash, melons, potatoes, cotton, beans, peas, grains, peanuts, sugarcane, beets, hops, tomatoes, and peppers.

15. The method defined in claim 12 wherein said solution further comprises a surfactant.

* * * * *